US006482645B2

(12) United States Patent
Atala

(10) Patent No.: US 6,482,645 B2
(45) Date of Patent: Nov. 19, 2002

(54) METHODS AND COMPOSITIONS FOR PRODUCING ARTIFICIAL FASCIA

(75) Inventor: Anthony Atala, Weston, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 10/090,892

(22) Filed: Mar. 5, 2002

(65) Prior Publication Data

US 2002/0094570 A1 Jul. 18, 2002

Related U.S. Application Data

(63) Continuation of application No. 09/474,391, filed on Dec. 29, 1999, now Pat. No. 6,368,859.

(30) Foreign Application Priority Data

Dec. 14, 2000 (WO) ............................. PCT/US00/33937

(51) Int. Cl.⁷ ................................................ C12N 5/00
(52) U.S. Cl. ..................... 435/395; 435/398; 435/401; 435/402; 424/93.7; 128/885; 128/898; 623/11.11
(58) Field of Search ..................... 435/395, 398, 435/401, 402; 128/885, 898; 424/93.7; 623/11.11

(56) References Cited

U.S. PATENT DOCUMENTS

| | | | |
|---|---|---|---|
| 4,458,678 A | 7/1984 | Yannas et al. | |
| 4,520,821 A | 6/1985 | Schmidt et al. | |
| 4,801,299 A | 1/1989 | Brendel et al. | |
| 4,963,489 A | 10/1990 | Naughton et al. | |
| 5,032,508 A | 7/1991 | Naughton et al. | |
| 5,160,490 A | 11/1992 | Naughton et al. | |
| 5,192,312 A | 3/1993 | Orton | |
| 5,443,950 A | 8/1995 | Naughton et al. | |
| 5,516,680 A | 5/1996 | Naughton et al. | |
| 5,567,612 A | 10/1996 | Vacanti et al. | |
| 5,613,982 A | 3/1997 | Goldstein | |
| 5,632,778 A | 5/1997 | Goldstein | |
| 5,753,267 A | 5/1998 | Badylak et al. | |
| 5,759,830 A | 6/1998 | Vacanti et al. | |
| 5,762,966 A | 6/1998 | Knapp, Jr. et al. | |
| 5,770,193 A | 6/1998 | Vacanti et al. | |
| 5,770,417 A | 6/1998 | Vacanti et al. | |
| 5,843,182 A | 12/1998 | Goldstein | |
| 5,851,833 A | 12/1998 | Atala | |
| 5,855,610 A | 1/1999 | Vacanti et al. | |
| 5,858,721 A | 1/1999 | Naughton et al. | |
| 5,863,531 A | 1/1999 | Naughton et al. | |
| 5,866,414 A | 2/1999 | Badylak et al. | |
| 5,899,936 A | 5/1999 | Goldstein | |
| 5,916,265 A | 6/1999 | Hu | |
| 5,962,325 A | 10/1999 | Naughton et al. | |
| 6,368,859 B1 * | 4/2002 | Atala ........................... | 435/395 |

FOREIGN PATENT DOCUMENTS

WO 8803785 6/1988

OTHER PUBLICATIONS

U.S. patent application Ser. No. 09/474,678, Atala et al., filed Dec. 1999.
U.S. patent application Ser. No. 09/474,525, Atala et al., filed Dec. 1999.
U.S. patent application Ser. No. 09/474,524, Atala et al., filed Dec. 1999.
da Silva, et al., "An In Vivo Model to Quantify Motor and Sensory Peripheral Nerve Regeneration Using Bioresorbable Nerve Guide Tubes," *Brain Research*, vol. 342, 1985, pp 307–315.
Michalopoulos, et al., "Primary Culture of Parenchymal Liver Cells on Collagen Membranes," *Experimental Cell Research*, vol. 94, 1975, pp 70–78.
Mooney, et al., "Tissue Engineering Using Cells and Synthetic Polymers," *Transplantation Reviews*, vol. 7, No. 3, Jul. 1993, pp 153–162.
Rosen et al., "Bioerodible Polyanhydrides for Controlled Drug Delivery," *Biomaterials*, vol. 4, Apr. 1983, pp 131–133.
Schmidt, "Acellular Vascular Tissues: Natural Biomaterials for Tissue Repair and Tissue Engineering," *Biomaterials*, vol. 21, 2000, pp 2215–2231.
Walton et al., "Tissue Engineering of Biomaterials for Composite Reconstruction: An Experimental Model," *Annals of Plastic Surgery*, vol. 30, No. 2, Feb. 1993, pp 105–110.
International Search Report, PCT/US00/33782, Apr. 5, 2001.

* cited by examiner

Primary Examiner—Leon B. Lankford, Jr.
(74) Attorney, Agent, or Firm—Thomas J. Engellenner; Jasbir Sagoo; Nutter McClennen & Fish LLP

(57) ABSTRACT

The present invention describes methods for producing artificial fascial slings and their subsequent use in treating subjects with urinary incontinence. The invention is based, in part, on the discovery that mesenchymal cells that secrete elastin and collagen, extracellular proteins responsible for elasticity and strength, respectively, can be used to engineer artificial fascia in vitro.

24 Claims, No Drawings

METHODS AND COMPOSITIONS FOR PRODUCING ARTIFICIAL FASCIA

REFERENCE TO RELATED APPLICATIONS

This application is a continuation of U.S. patent application Ser. No. 09/474,391, filed Dec. 29, 1999, now U.S. Pat. No. 6,368,859 the content of which are expressly incorporated by reference.

BACKGROUND OF THE INVENTION

The technical field of the invention is the treatment of urinary incontinence. It is known in the act of surgery that one can treat patients with stress urinary incontinence by constructing a sling to support the bladder. The slings are usually designed to prevent leakage by providing circumferential pressure at the level of the bladder neck. The construction of such slings typically involves rotating various muscles and their attendant fascias (Mohenfellnev (1986) *Sling Procedures in Surgery*, In Stanton SI, Tanaglo E (eds) *Surgery of Female Incontinence,* 2nd edn, Berlin; Springer-Vevlag).

Many natural and synthetic materials have been used to construct these slings, such as the Martex sling (Morgan, et al. (1985) *Amer. J. Obst. Gynec.* 151:224–226); the fascia lata sling (Beck, et al. (1988) *Obst. Gynec.* 72:699–703); the vaginal wall sling (Juma, et al. (1992) *Urology,* 39:424–428); the Aldridge sling (McIndoe et al. (1987)*Aust. N. Z. J. Obst. Gynaecol.* 27: 238–239); and the Porcine corium sling (Josif (1987) *Arch. Gynecol.* 240:131–136). Slings have also been produced from allogenic grafts, particularly if the patient has poor quality fascia.

There are however, a number of problems associated with using these procedures and materials. Problems associated with using natural material as slings include, shrinkage, necrosis, and gradual thinning of the fascia which ultimately affects the efficiency and long term durability of the sling (Blaivas (1991) *J. Urol.* 145:1214–1218). Another major disadvantage with using natural material is that extensive surgery is required, which can cause morbidity, typically as a result of nerve damage or wound infection (McGuire, et al. (1978) *J. Urol.* 119:82–84; Beck, et al. (1974) *Am. J. Obstet. Gynecol.* 129:613–621.) In addition, natural slings obtained from human donors carry with them the added risk of causing an immune reaction in the recipient.

As an alternative, synthetic materials have been used in patients who had poor quality, or insufficient fascial tissue for reconstructive purposes. However, reports of graft rejection, sinus formation, urethral obstruction and urethral erosion have limited the widespread use of these materials (See e.g, Nichols (1973) *Obstet. Gynecol.* 41:88–93; Morgan, et al. (1985) *Am. J. Obstet.* 151:224–226; and Chin et al. (1995) *Br. J. Obstet. Gyneacol.,* 102:143–147.)

Accordingly, there exists a need to produce artificial fascial slings to treat urinary incontinence without the need of extensive surgery. There is also a need to produce artificial fascial slings which do not result in the disadvantages associated with synthetic materials used as fascial slings to date.

SUMMARY OF THE INVENTION

The present invention provides methods for producing artificial fascial slings and their subsequent use in treating subjects with urinary incontinence. The invention is based, in part, on the discovery that mesenchymal cells that secrete elastin and collagen, two extracellular proteins responsible for elasticity and strength, respectively, can be used to engineer artificial fascia in vitro.

Accordingly, in one aspect, the invention features a method for producing an artificial fascial sling comprising:
  creating a polylayer of collagen-secreting cells derived from a cultured cell population on a biocompatible substrate; and
  creating a polylayer of elastin-secreting cells derived from a second cultured cell population on the polylayer of the collagen-secreting cells, such that the cells of the two different populations form a chimeric interface.

The invention can further include the step of creating a fibroblast polylayer derived from a cultured fibroblast cell population on the polylayer of elastin-secreting cells, such that the fibroblast polylayer forms a chimeric interface with the polylayer of elastin-secreting cells.

The substrate is preferably a strip having a length of about 10 cm to about 30 cm, and a width of about 0.5 cm to about 4.0 cm. The strip can further include attachment sites that provide attachment to a support surface.

The method further comprising selecting a biocompatible substrate from the group consisting of cellulose ether, cellulose, cellulosic ester, fluorinated polyethylene, phenolic, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polymide, polyolefin, polyoxadiazole, polyphenylene oxide, polyphenylene, sulfide, polypropylene, polystyrene, polysulfide, polysulfone, polytetrafluoroethylene, polythioether, polytriazole, polyurethane, polyvinylidene fluoride, regenerated cellulose, urea-formaldehyde, or copolymers or physical blends thereof. In one preferred embodiment, the biocompatable substrate is polyglycolic acid.

In one embodiment, the collagen-secreting cells are selected from the group consisting of fibroblasts, chondroblasts, osteoblasts, and odontoblasts. In another embodiment, the elastin-secreting cells are selected from the group consisting of smooth muscle cells, chondrocytes, and fibroblasts.

In another aspect, the invention features a method for producing an artificial fascial sling comprising:
  creating a polylayer of a collagen-secreting cells derived from a cultured cell population on a first surface of a biocompatible substrate; and
  creating a polylayer of elastin-secreting cells derived from a second cultured cell population on a second surface of the biocompatible substrate, wherein the second surface is opposite the first surface.

The invention can further include the step of creating a fibroblast polylayer derived from a cultured fibroblast cell population, such that the fibroblast polylayer forms a chimeric interface with the at least one polylayer selected from the group consisting of a collagen polylayer or an elastin polylayer.

In yet another aspect, the invention features a method for treating a subject with urinary incontinence with an artificial fascial sling comprising:
  positioning the artificial fascial sling around a urinary structure, the artificial sling comprising a polylayer of collagen-secreting cells derived from a cultured cell population deposited on a biocompatible substrate, and a polylayer of elastin-secreting cells derived from a second cultured cell population deposited on the polylayer of collagen-secreting cell population, such that the cells of the two different populations form a chimeric interface;

moving the urinary structure to a position that ameliorates urinary incontinence; and securing the artificial fascial sling in a position that supports the urinary structure, to thereby treat a subject with urinary incontinence.

Optionally, a fibroblast polylayer, derived from a cultured fibroblast cell population, can be deposited on the polylayer of elastin-secreting cells, such that the fibroblast polylayer forms a chimeric interface with the polylayer of elastin-secreting cells. In one embodiment, the method further comprising altering the tension of the artificial fascial sling to change the position of the urinary structure. In another embodiment, the step of positioning the artificial fascial sling around a urinary structure further comprises positioning the artificial fascial sling around a bladder. In another embodiment, the step of positioning an artificial fascial sling around a urinary structure comprises positioning the artificial fascial sling around a urethra. In yet another embodiment, the step positioning an artificial fascial sling around a urinary structure comprises positioning the artificial fascial sling around a ureter.

In one embodiment, the step of securing the artificial fascial sling to a support structure comprises securing the artificial fascial sling with a securing agent. The securing agent can be selected from the group consisting of felt matrix, mesh patch and/or sutures.

In another embodiment, the step of securing the artificial fascial sling to a support structure comprises securing the artificial sling to a support structure selected from the group consisting of the pubis bone, pelvic bone and inferior pubic arch.

DETAILED DESCRIPTION

So that the invention may more readily be understood, certain terms are first defined:

The term "polylayer" as used herein refers to an arrangement comprising multiple layers of a homogenous cultured cell population superimposed over each other. The process of producing a "polylayer" involves depositing one layer of a cell population on surface, e.g., a biocompatible substrate. The deposited cells are cultured in growth medium until they develop and proliferate to produce a monolayer comprising cells with a desired phenotype and morphology. Once the first monolayer has attained a desired cell density, a second layer of the same cell population is depositing on the first monolayer. The second layer of deposited cells are cultured in growth medium which supplies nutrients to both the second cell layer and the first monolayer, until the cells in the second layer develop and proliferate to a desired cell density to produce a bilayer having cells with a desired phenotype and morphology. A third layer of same cell population can be deposited on the bilayer, and the cells are cultured in growth medium which supplies nutrients to the bilayer and the cells of the third layer, until the cells of the third layer develop and proliferate to a desired density to produce a trilayer with a desired phenotype and morphology. The process can be repeated until a polylayer comprising many layers of a homogenous cell population is produced. The characteristics of the polylayer are such that they closely resemble the morphology and functional characteristics of the equivalent parenchyma tissue of an in-vivo organ. For example, a polylayer comprising a smooth muscle cell population may have functional characteristics of the smooth muscle tissue of a bladder, i.e., the detrusor.

The term "chimeric interface" as used herein refers to the boundary formed between two different cell populations. Chimeric interface is also intended to include the boundary formed between a cell population and a non-cell population, for example, a fibroblast cell population and isolated collagen.

The term "interstitial biomaterial" as used herein refers to the formation of cellular material at the chimeric interface where two different cell populations are in mutual contact with each other. The term "interstitial biomaterial" in its broadest concept is intended to include the formation of any new cellular material formed when two or more different cell populations are in contact with each other. The new cellular material resembles the equivalent cellular material produced in normal in-vivo cellular development of the organ.

The term "biocompatible substrate" as used herein refers to a material that is suitable for implantation into a subject onto which a cell population can be deposited. A biocompatible substrate does not cause toxic or injurious effects once implanted in the subject.

The term "collagen-secreting cells" is intended to refer to cells that produce collagen such as, mesenchymal cells, for example, fibroblasts, chondroblasts, osteoblasts, and odontoblasts. Collagen that has been extracted from a mammalian source, such as collagen extracted from skin and tendons, can also be deposited on the biocompatible substrate.

The term "elastin-secreting cells" is intended to refer to cells that produce elastin such as, mesenchymal cells, for example, smooth muscle cells, chondrocytes, and fibroblasts. Elastin that has been extracted from mammalian source, such as elastin extracted from skin, can also be deposited on the biocompatible substrate.

The term "subject" as used herein is intended to include living organisms in which an immune response is elicited. Preferred subjects are mammals. Examples of subjects include, but are not limited to, humans, monkeys, dogs, cats, mice, rats, cows, horses, pigs, goats and sheep.

The term "urinary structure" as used herein refers to a structure responsible for urinary incontinence that requires repositioning using an artificial sling. Repositioning the urinary structure results in amelioration of urinary incontinence. Examples of urinary structure include, but are not limited to the bladder, urethra and ureter.

Various aspects of the invention are described in more detail in the following subsections:

I. Biocompatible Substrates

A biocompatible substrate refers to materials which do not have toxic or injurious effects on biological functions. Examples of biocompatible substrates include, but are not limited to, polyglycolic acid and polyglactin, developed as absorbable synthetic suture material. Polyglycolic acid and polyglactin fibers may be used as supplied by the manufacturer. Other biodegradable materials include cellulose ether, cellulose, cellulosic ester, fluorinated polyethylene, phenolic, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polylmide, polyolefin, polyoxadiazole, polyphenylene oxide, polyphenylene, sulfide, polypropylene, polystyrene, polysulfide, polysulfone, polytetrafluoroethylene, polythioether, polytriazole, polyurethane, polyvinylidene fluoride, regenerated cellulose, urea-formaldehyde, or copolymers or physical blends of these materials. The material may be impregnated with suitable antimicrobial agents and may be colored by a color additive to improve visibility and to aid in surgical procedures.

II. Culturing Cells

One aspect of the invention pertains to production of artificial slings comprising one or more cell populations. The artificial slings can be allogenic artificial slings, where the cultured cell populations are derived from the subject's own tissue. The artificial slings can also be xenogenic, where the cultured cell populations are derived form a mammalian species that is different from the subject. For example the cells can be derived from organs of mammals such as monkeys, dogs, cats, mice, rats, cows, horses, pigs, goats and sheep.

Cells can be isolated from a number of sources, for example, from biopsies, or autopsies. The isolated cells are preferably autologous cells, obtained by biopsy from the subject. For example, a biopsy of smooth muscle from the area treated with local anaesthetic with a small amount of lidocaine injected subcutaneously. The cells from the biopsied tissue can be expanded in culture. The biopsy can be obtained using a biopsy needle, a rapid action needle which makes the procedure quick and simple. The small biopsy core can then be expanded and cultured, as described by Atala, et al., (1992) *J. Urol.* 148, 658–62; Atala, et al. (1993) *J. Urol.* 150: 608–12, incorporated herein by reference. Cells from relatives or other donors of the same species can also be used with appropriate immunosuppression, for example, endothelial cells from dissected veins, or fibroblast cells from foreskins (see examples 1 and 2, respectively).

Dissociation of the cells to the single cell stage is not essential for the initial primary culture because single cell suspension may be reached after a period of in vitro culture. Tissue dissociation may be performed by mechanical and enzymatic disruption of the extracellular matrix and the intercellular junctions that hold the cells together. Preferred cell types include, but are not limited to, mesenchymal cells, especially smooth muscle cells, skeletal muscle cells, myocytes (muscle stem cells), fibroblasts, chondrocytes, osteoblasts, chondroblasts, ondoblasts, adipocytes, fibromyoblasts, and ectodermal cells, including ductile and skin cells, hepatocytes, and other parenchymal cells. In a preferred embodiment, fibroblast cells are isolated.

Cells can be cultured in vitro to increase the number of cells available for coating the biocompatible substrate. The use of allogenic cells, and more preferably autologous cells, is preferred to prevent tissue rejection. However, if an immunological response does occur in the subject after implantation of the artificial organ, the subject may be treated with immunosuppressive agents such as, cyclosporin or FK506, to reduce the likelihood of rejection. In certain embodiments, chimeric cells, or cells from a transgenic animal, can be coated onto the biocompatable substrate.

Cells may be transfected with genetic material prior to coating. Useful genetic material may be, for example, genetic sequences which are capable of reducing or eliminating an immune response in the host. For example, the expression of cell surface antigens such as class I and class II histocompatibility antigens may be suppressed. This may allow the transplanted cells to have reduced chance of rejection by the host. In addition, transfection can also be used for gene modification.

Cell cultures may be prepared with or without a cell fractionation step. Cell fractionation may be performed using techniques, such as flourescent activated cell sorting, which are known in the art. Cell fractionation may be performed based on cell size, DNA content, cell surface antigens, and for viability.

The isolated cells can be normal or can manipulated genetically to provide additional functions. Methods for genetically engineering cells with retroviral vectors, polyethylene glycol, or other methods known to those skilled in the art can be used. These include using expression vectors which transport and express nucleic acid molecules in the cells. (See Goeddel; *Gene Expression Technology: Methods in Enzymology* 185, Academic Press, San Diego, Calif. (1990), incorporated herein by reference). Vector DNA can be introduced into cells via conventional transformation or transfection techniques. Suitable methods for transforming or transfecting host cells can be found in Sambrook et al. (*Molecular Cloning: A Laboratory Manual,* 2nd Edition, Cold Spring Harbor Laboratory press (1989), incorporated herein by reference), and other laboratory textbooks.

III. Production of Artificial Slings

In one aspect, the invention features methods of producing artificial slings using one or more cultured cell populations on a biocompatible substrate. Cells can be expanded as described in Section II, and used to create polylayers on a biocompatible substrate. The cultured cell populations can be used to produce heterogenous polylayers on one or more surface(s) of a biocompatible substrate. Examples of suitable biocompatible substrates are described in Section I.

In one embodiment, one surface of the biocompatible substrate is used to produce the artificial sling. This can be performed by depositing a suspension of a collagen-secreting cell population (e.g., mesenchymal cells such as, fibroblasts, chondroblasts, osteoblasts and ondoblasts.) one side of the biocompatible substrate. The collagen-secreting cells are incubated until the cells develop and proliferate to produce at least a monolayer of cells. A second suspension of collagen-secreting cells can then be deposited on the first layer, and the cells are incubated until they develop and proliferate to produce a bilayer. The process is repeated to produce a polylayer of collagen-secreting cells.

In another embodiment, collagen can be added to the biocompatible substrate. For example, collagen can be derived from any number of mammalian sources, typically bovine, porcine, or ovine skin and tendons. The collagen can be acid-extracted from the collagen source using a weak acid, such as acetic, citric, or formic acid. Once extracted into solution, the collagen can be salt-precipitated using NaCl and recovered, using standard techniques such as centrifugation or filtration. Details of acid extracted collagen are described, for example, in U.S. Pat. No. 5,106,949, issued to Kemp et al. incorporated herein by reference.

In another embodiment, additional collagen can be added between the heterogenous polylayers to promote growth and development between the cells of heterogeneous polylayers. In yet another embodiment, factors such as nutrients, growth factors, cytokines, extracellular matrix components, inducers of differentiation or dedifferentiation, products of secretion, immunomodulation, and/or biologically active compounds which enhance or allow growth of the cellular network can be added between the heterogenous polylayers.

After the collagen polylayer is established, an elastin polylayer can be created using a suspension of an elastin-secreting cell population (e.g. smooth muscle cells, chondrocytes, and fibroblasts.) Cells of the elastin-secreting cells are incubated until the cells develop and proliferate to produce at least a monolayer of cells. A second suspension of the elastin-secreting cells are then deposited on the first layer, and the cells are incubated until they develop and proliferate to produce a bilayer. The process is repeated to produce a polylayer of elastin-secreting cells.

A chimeric interface is produced where two or more heterogenous polylayers are in mutual contact with each other. This enables unhindered interaction to occur between the cells of the polylayers. Extensive interactions between different cell populations results in the production of a interstitial material, which can develop into an interstitial biomaterial that is different from each of the polylayers. The interstitial biomaterial can provide unique biological and functional properties to the artificial sling.

The skilled artisan will appreciate that any interstitial biomaterial produced when two or more heterogenous polylayers comprising different cell populations interact, is within the scope of the invention. The different interstitial biomaterial produced will depend on the type of cells in the heterogenous polylayer.

In another embodiment, at least two surfaces of the biocompatible substrate are used to produce the artificial sling. This can be performed by depositing a suspension of a collagen-secreting cells (e.g., mesenchymal cells such as, fibroblasts, chondroblasts, osteoblasts and ondoblasts.) on one surface of the biocompatible substrate. The collagen-secreting cells are incubated until the cells develop and proliferate to produce a monolayer of cells. The process is repeated to produce a polylayer of collagen-secreting cells. Next, a suspension of an elastin-secreting cells (e.g., smooth muscle cells, chondrocytes, and fibroblasts) can be deposited on a second surface that is opposite the first surface of a biocompatible substrate. The elastin-secreting cells are incubated until the cells develop and proliferate to produce a monolayer of cells. The process is repeated to produce a polylayer of elastin-secreting cells.

The skilled artisan will appreciate that the length and width of the artificial sling can be selected based on the size of the subject and the urinary structure which requires positioning to ameliorate urinary incontinence. The length and width of the artificial sling can easily be altered by shaping the biocompatible substrate to a desired length and width. In one embodiment, the artificial fascial sling has a biocompatible substrate with a length (defined by a first and second long end) of about 10 cm to about 30 cm. The artificial fascial sling can further have a length of about 15 cm to about 25 cm. In a preferred embodiment, the artificial fascial sling includes a biocompatible substrate with a length of about 20 cm. In another embodiment, the biocompatible substrate has a width (defined by a first and second short end) of about 0.5 cm to about 4.0 cm. The artificial fascial sling can further have a width of about 1.0 cm to about 3.0 cm. In a preferred embodiment, the artificial fascial sling has a biocompatible substrate with width of about 2.0 cm.

The artificial sling can be secured to a support structure in the subject. The support structure for securing the artificial sling can be selected based on the anatomy of the subject, for example, the support structure for a male subject may be different from the support structure of a female subject. Examples of support structures include, but are not limited to, the pubis bone, pelvic bone and inferior pubic arch.

The artificial sling can be secured to the support structure with a securing agent Examples of securing agents include, but are not limited to, felt matrix, mesh patch and for sutures. Techniques for attaching the artificial sling to the support structure are known in the art (See e.g., Horbach et al. (1988) *Obst. and Gyn.* 71: 648–652; Raz et al. (1988) *J. Urol.* 139:528–531; Mickey et al. (1990) *Obst. and Gyn.* 75: 461–463; Handa et al. (1996), *Obst. and Gyn.* 88: 1045–1049: Barbalias et al. (1997) *Eur. Urol,* 31: 394–400; Govier et al. (1997) *J. Urol.* 157: 117–121; Jorion (1997) *J. Urol.* 157: 926–928; Wright et al. (1998) *J. Urol.* 160: 759–762, all incorporated herein by reference).

The tension of the artificial sling positioned around the urinary structure can also be adjusted to provide the required amelioration of incontinence. The can be performed, for example, by tacking the artificial fascial sling onto itself, which provides the ability to change the tension of the artificial sling in small increments and also moves the urinary structure to the desired position.

In another embodiment, the invention can also be used to produce an artificial fascial patch that can be attached to the base of the bladder and urethra. The artificial fascial patch can then be secured to a support structure in the subject to reposition the base of the bladder and urethra such that ameliorate urinary incontinence is ameliorated.

Urodynamic evaluations can be conducted to determine the extent of amelioration of urinary incontinence. Methods for urodynamic evaluation are known in the art and include for example, videourodynamics with intravascular and intraurethral pressure measurements (See e.g., Barbalias et al. (1997) *Eur. Urol.,* 31: 394–400).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

EXAMPLES

Example 1

In vitro Culturing of Fibroblast Cells

This example describes one of many possible methods of isolating and culturing fibroblast cells. Dermal tissue was isolated from foreskin and cut into 2–3 mm sized fragments. The fragments were placed onto a 100 mm cell culture plate and allowed to adhere to the plate for approximately 10 min. After the fragments had adhered to the plate, 15 ml of culture medium (Dulbecco's Modified Eagle Media (DMEM, HyClone Laboratories, Inc., Logan, Utah) with 10% fetal bovine serum (FBS, Gibco) and penicillin/streptomycin (Sigma, St. Louis, Mo.)), was added and the plates were incubated undisturbed for 5 days at 37° C. with 5% $CO_2$. When small island of fibroblast cells appeared, the culture medium was changed and non-adherent tissue fragments were removed. Adhered fibroblast cells were incubated until a sufficient number of fibroblast cells had formed. These fibroblast cells were trypsinized, counted and plated onto 100 mm plates containing 10 ml media for further expansion. The media was changed every 3 days depending on the cell density. Fibroblast cells were cultured until they were approximately 80–90% confluent.

Fibroblast cells were passaged by removing the culture medium, adding 10 ml PBS/EDTA (1 liter of 1X PBS containing 530 mL, 0.5M EDTA, with the pH adjusted to pH 7.2 with 1M HCl and filter sterilized) and incubating for 4 minutes. The separation of the cells was confirmed using a phase contrast microscope. After 4 minutes of incubation, the PBS/EDTA solution was removed and replaced with 5 ml Trypsin/EDTA (0.05% trypsin, 0.53 mM EDTA) to disperse the cells. The dispersed cells were plated into 10 ml culture dishes with a total cell and culture medium volume of 10 ml. The fibroblast cells were expanded until sufficient cell quantities were achieved. Cells were then trypsinized, collected, washed and counted for seeding.

Example 2

In vitro Culturing of Endothelial Cells

Endothelial cells, were isolated form a dissected vein. Perivenous heparin/papaverine solution (3 mg papaverine HCl diluted in 25 ml Hanks balanced salt solution (HBSS) containing 100 units of heparin (final conc. 4 u/ml)), was used to improve endothelial cell preservation. A proximal silk loop was placed around the vein and secured with a tie. A small venotomy was made proximal to the tie and the tip of vein cannula was inserted and secured in place with a second tie. A second small venotomy was made beyond the proximal tie and the vein was gently flushed with Medium 199/heparin solution Medium 199 (M-199) supplemented with 20% fetal bovine serum, ECGF (100 mg/ml), L-glutamine, heparin (Sigma, 17.5 u/ml) and antibioticantimycotic), to remove blood and blood clots. Approximately 1 ml of a collagenase solution (0.2% Worthington type I collagenase dissolved in 98 ml of M-199, 1 ml of FBS, 1 ml of PSF, at 37° C. for 15–30 min, and filter sterilized), was used to flush through the dissected vein. The collagenase solution was also used to gently distend the vein and the distended vein was placed into 50 ml tube containing Hank's Balanced Salt Solution (HBSS). The tube containing the collagenase distended vein was incubated for 12 minutes at 37° C. to digest the inner lining of the vein. After digestion, the contents of the vein, which contain the endothelial cells, were removed into a sterile 15 ml tube. The endothelial cell suspension was centrifuged at 125×g for 10 minutes. Endothelial cells were resuspended in 2 ml of Dulbec Co.'s Modified Eagle Media with 10% FBS and penicillin/streptomycin (DMEM/10%FBS) and plated into a 24 well plate coated with 1% difcogelatin. The endothelial cells were incubated overnight at 37° C.

After overnight incubation, the cells were rinsed with HBSS and placed in 1 ml of fresh DMEM/10%FBS. The media was changed 3 times a week. When cultures reached confluence (after 3–7 days), the confluent monolayers were subcultured by treatment with 0.05% trypsin, 0.53 mM EDTA, for 3–5 min until the cells dispersed. The dispersed cells were plated onto culture dishes coated with 0.1% difcogelatin at a 1:4–1:6 split ratio. The endothelial cells were expanded until sufficient cell quantities were achieved. Cells were trypsinized, collected, washed and counted for seeding.

Example 3

Creation of an Artificial Fascial Sling

A synthetic polymer matrix of polyglycolic acid was cut to an average length of about 15 cm and a width of about 2 cm. The polyglycolic acid matrix was coated with a liquified copolymer, at a mixture of about 50% poly-DL-lactate-co-glucoside and about 50% 80 mg/ml methylene chloride, to obtain the desired mechanical characteristics. After sterilization, the polymer was stored in a desiccator until ready for use.

For each fascial sling, about 32 confluent 25 cm plates of each cell type, collagen-secreting cells, elastin-secreting cells and fibroblast cells, were processed for coating onto the polyglycolic acid matrix. The cells were resuspended in culture medium and applied at a cell density of about 107 cells/ml to one surface of the polymer matrix. The coated polymer was incubated in Dulbeccos's Modified Eagles Medium (DMEM, Sigma, St. Louis, Mo.) supplemented with 10% fetal calf serum (Biowhittaker Inc., Walkersville, Md.). The medium was changed at 12 hour intervals to ensure sufficient supply of nutrients. The cells were cultured until they attached to the surface of the polymer and began to grow and develop. A second suspension collagen-secreting cells was then coated onto the existing collagen layer. The cells were incubated until they grew and developed into a layer of collagen cells. The process was repeated until a polylayer of collagen developed.

The elastin-secreting cell population was coated onto the collagen polylayer. The cells were incubated until they formed an interface with the collagen polylayer and developed into a monolayer of elastin cells. A second suspension of elastin-secreting cells was then applied to the elastin monolayer and allowed to develop into a second monolayer. The process was repeated until a polylayer of elastin cells developed over the polylayer of collagen cells. Finally, a population of fibroblast cells was coated onto the polylayer of elastin-secreting cells. The cells were cultured until they developed into a monolayer of fibroblast cells. A second suspension of fibroblast cells was applied to the monolayer of fibroblast cells, and the cells were cultured until they grew and developed to form a second monolayer. The process was repeated until a polylayer of fibroblasts was formed.

What is claimed:

1. An artificial fascia comprising:
    a polylayer of collagen-secreting cells derived from a cultured cell population on a biocompatible substrate; and
    a polylayer of elastin-secreting cells derived from a second cultured cell population on the polylayer of the collagen-secreting cell population, such that the cells of the two different populations form a chimeric interface.

2. The artificial fascia of claim 1, further comprising a fibroblast polylayer derived from a cultured fibroblast cell population such that the fibroblast polylayer forms the chimeric interface with the polylayer of collagen secreting cells.

3. The artificial fascia of claim 1, further comprising selecting a biocompatable substrate from the group consisting of cellulose ether, cellulose, cellulosic ester, fluorinated polyethylene, phenolic, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polymide, polyolefin, polyoxadiazole, polyphenylene oxide, polyphenylene, sulfide, polypropylene, polystyrene, polysulfide, polysulfone, polytetrafluoroethylene, polythioether, polytriazole, polyurethane, polyvinylidene fluoride, regenerated cellulose, urea-formaldehyde, or copolymers or physical blends thereof.

4. The artificial fascia of claim 1, further comprising selecting a polyglycolic acid biocompatable substrate.

5. The artificial fascia of claim 1, wherein the collagen-secreting cells are selected from the group consisting of fibroblasts, chondroblasts, osteoblasts, and odontoblasts.

6. The artificial fascia of claim 1, wherein the elastin-secreting cells are selected from the group consisting of smooth muscle cells, chondrocytes, and fibroblasts.

7. An artificial fascia comprising:
    a polylayer of a collagen-secreting cells derived from a cultured cell population on a first surface of a biocompatible substrate; and a polylayer of elastin-secreting cells derived from a second cultured cell population on a second surface of the biocompatible substrate, wherein the second surface is opposite the first surface.

8. The artificial fascia of claim 7 further comprising a fibroblast polylayer derived from a cultured fibroblast cell population such that the fibroblast polylayer forms a chimeric interface with at least one polylayer selected from the group consisting of a collagen polylayer or an elastin polylayer.

9. The artificial fascia of claim 7, further comprising selecting a biocompatable substrate from the group consisting of cellulose ether, cellulose, cellulosic ester, fluorinated polyethylene, phenolic, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polymide, polyolefin, polyoxadiazole, polyphenylene oxide, polyphenylene, sulfide, polypropylene, polystyrene, polysulfide, polysulfone, polytetrafluoroethylene, polythioether, polytriazole, polyurethane, polyvinylidene fluoride, regenerated cellulose, urea-formaldehyde, or copolymers or physical blends thereof.

10. The artificial fascia of claim 7, further comprising selecting a polyglycolic acid biocompatable substrate.

11. The artificial fascia of claim 7, wherein the collagen-secreting cells are selected from the group consisting of fibroblasts, chondroblasts, osteoblasts, and odontoblasts.

12. The artificial fascia of claim 7, wherein the elastin-secreting cells are from the group consisting of smooth muscle cells, chondrocytes, and fibroblasts.

13. A method for producing an artificial fascia comprising:
creating a polylayer of collagen-secreting cells derived from a cultured cell population on a biocompatible substrate; and
creating a polylayer of elastin-secreting cells derived from a second cultured cell population on the polylayer of the collagen-secreting cell population, such that the cells of the two different populations form a chimeric interface.

14. The method of claim 13, wherein the method further comprises creating a fibroblast polylayer derived from a cultured fibroblast cell population such that the fibroblast polylayer forms the chimeric interface with the polylayer of collagen secreting cells.

15. The method of claim 13, further comprising selecting a biocompatable substrate from the group consisting of cellulose ether, cellulose, cellulosic ester, fluorinated polyethylene, phenolic, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polymide, polyolefin, polyoxadiazole, polyphenylene oxide, polyphenylene, sulfide, polypropylene, polystyrene, polysulfide, polysulfone, polytetrafluoroethylene, polythioether, polytriazole, polyurethane, polyvinylidene fluoride, regenerated cellulose, urea-formaldehyde, or copolymers or physical blends thereof.

16. The method of claim 13, further comprising selecting a polyglycolic acid biocompatable substrate.

17. The method of claim 13, wherein the collagen-secreting cells are selected from the group consisting of fibroblasts, chondroblasts, osteoblasts, and odontoblasts.

18. The method of claim 13, wherein the elastin-secreting cells are selected from the group consisting of smooth muscle cells, chondrocytes, and fibroblasts.

19. A method for producing an artificial fascia comprising:
creating a polylayer of a collagen-secreting cells derived from a cultured cell population on a first surface of a biocompatible substrate; and
creating a polylayer of elastin-secreting cells derived from a second cultured cell population on a second surface of the biocompatible substrate, wherein the second surface is opposite the first surface.

20. The method of claim 19, wherein the method further comprises creating a fibroblast polylayer derived from a cultured fibroblast cell population such that the fibroblast polylayer forms a chimeric interface with at least one polylayer selected from the group consisting of a collagen polylayer or an elastin polylayer.

21. The method of claim 19, further comprising selecting a biocompatable substrate from the group consisting of cellulose ether, cellulose, cellulosic ester, fluorinated polyethylene, phenolic, poly4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polymide, polyolefin, polyoxadiazole, polyphenylene oxide, polyphenylene, sulfide, polypropylene, polystyrene, polysulfide, polysulfone, polytetrafluoroethylene, polythioether, polytriazole, polyurethane, polyvinylidene fluoride, regenerated cellulose, urea-formaldehyde, or copolymers or physical blends thereof.

22. The method of claim 19, further comprising selecting a polyglycolic acid biocompatable substrate.

23. The method of claim 19, wherein the collagen-secreting cells are selected from the group consisting of fibroblasts, chondroblasts, osteoblasts, and odontoblasts.

24. The method of claim 19, wherein the elastin-secreting cells are from the group consisting of smooth muscle cells, chondrocytes, and fibroblasts.

* * * * *